US009717877B2

(12) United States Patent
Satoh et al.

(10) Patent No.: US 9,717,877 B2
(45) Date of Patent: Aug. 1, 2017

(54) APPARATUS FOR SUPPLYING HIGH-CONCENTRATION HYDROGEN GAS FOR LIVING ORGANISM

(71) Applicant: MIZ Co., Ltd., Kanagawa (JP)

(72) Inventors: Fumitake Satoh, Kanagawa (JP); Ryousuke Kurokawa, Kanagawa (JP); Bunpei Satoh, Kanagawa (JP); Tomoki Seo, Kanagawa (JP)

(73) Assignee: MIZ Co., Ltd., Kanagawa (JP)

( * ) Notice: Subject to any disclaimer, the term of this patent is extended or adjusted under 35 U.S.C. 154(b) by 298 days.

(21) Appl. No.: 14/405,109

(22) PCT Filed: May 22, 2013

(86) PCT No.: PCT/JP2013/064175
§ 371 (c)(1),
(2) Date: Dec. 2, 2014

(87) PCT Pub. No.: WO2013/183448
PCT Pub. Date: Dec. 12, 2013

(65) Prior Publication Data
US 2015/0144132 A1    May 28, 2015

(30) Foreign Application Priority Data

Jun. 4, 2012 (JP) ................................ 2012-127296
Aug. 9, 2012 (JP) ................................ 2012-176861

(51) Int. Cl.
*A61M 11/00* (2006.01)
*A61M 16/12* (2006.01)
(Continued)

(52) U.S. Cl.
CPC ...... *A61M 16/125* (2014.02); *A61M 16/0057* (2013.01); *A61M 16/122* (2014.02);
(Continued)

(58) Field of Classification Search
CPC ............ A61M 16/125; A61M 16/0057; A61M 2202/02; A61M 2205/82; A61M 16/0672;
(Continued)

(56) References Cited

U.S. PATENT DOCUMENTS

2007/0227905 A1* 10/2007 Akahori ................. B01D 61/44
                                                                  205/772
2011/0111048 A1*  5/2011 Satoh ................... A61M 1/1656
                                                                  424/529
2015/0292091 A1* 10/2015 Satoh ....................... C25B 1/04
                                                                  204/265

FOREIGN PATENT DOCUMENTS

JP         9-186133 A       7/1997
JP      2005087257 A        4/2005
(Continued)

OTHER PUBLICATIONS

Office Action mailed Aug. 3, 2015 in corresponding Chinese Application No. 201380029653.6.

*Primary Examiner* — Steven Douglas
(74) *Attorney, Agent, or Firm* — Muncy, geissler, Olds & Lowe, P.C.

(57) ABSTRACT

An apparatus includes an electrolytic cell having an electrolytic chamber to which subject raw water is introduced, at least one membrane that separates inside and outside of the electrolytic chamber, and at least one pair of electrode plates provided in the inside and the outside of the electrolytic chamber so as to sandwich the membrane, the electrode plate in the outside of the electrolytic chamber being provided to be in contact with the membrane; a direct-current power source that applies a direct-current voltage to the pair of electrode plates; and a diluent gas supplier for diluting hydrogen gas generated from the electrode plate that is to be a cathode, wherein the apparatus blows diluent gas supplied from the diluent gas supplier to the cathode thereby to
(Continued)

constantly maintain a hydrogen gas concentration in the vicinity of the cathode during electrolysis at lower than 18.3 vol % so that mixed gas comprising the hydrogen gas and the diluent gas and having a hydrogen gas concentration of 0.1 to 18.3 vol % is supplied to a living organism.

20 Claims, 1 Drawing Sheet

(51) Int. Cl.
    *C25B 15/08*     (2006.01)
    *C25B 1/04*     (2006.01)
    *A61M 16/00*     (2006.01)
    *A61M 16/06*     (2006.01)

(52) U.S. Cl.
    CPC ............... *C25B 1/04* (2013.01); *C25B 15/08* (2013.01); *A61M 16/0672* (2014.02); *A61M 2202/02* (2013.01); *A61M 2202/0468* (2013.01); *A61M 2205/70* (2013.01); *A61M 2205/82* (2013.01); *Y02E 60/366* (2013.01)

(58) Field of Classification Search
    CPC ............ A61M 16/122; A61M 2205/70; A61M 2202/0468; C25B 1/08; C25B 11/02; C25B 9/08; C25B 15/08; Y02E 60/366
    See application file for complete search history.

(56) References Cited

FOREIGN PATENT DOCUMENTS

| | | |
|---|---|---|
| JP | 2005097667 | 4/2005 |
| JP | 2009-005881 A | 1/2009 |
| JP | 2009-228044 A | 10/2009 |
| WO | WO2011/004343 A1 | 1/2011 |

* cited by examiner

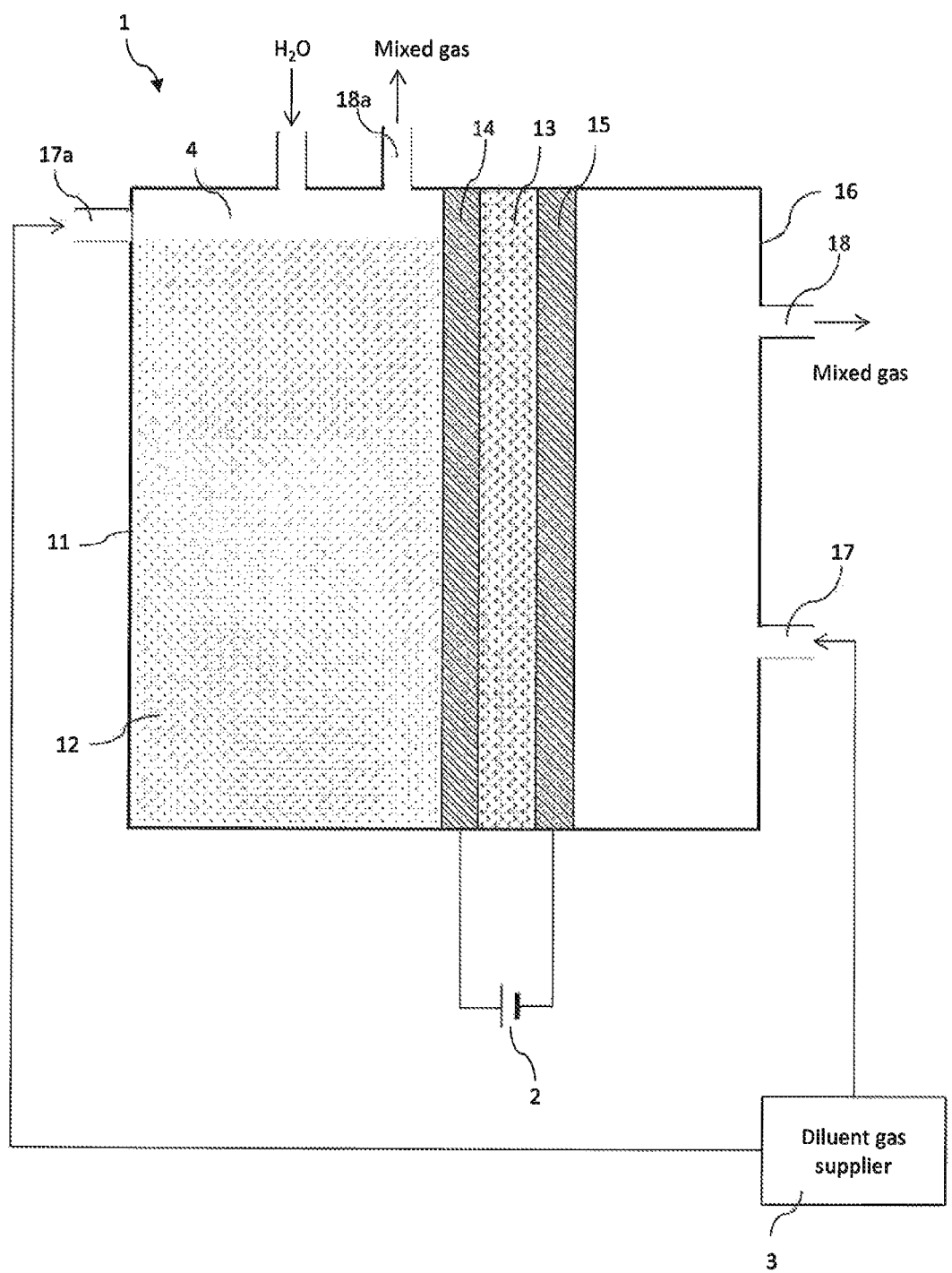

APPARATUS FOR SUPPLYING HIGH-CONCENTRATION HYDROGEN GAS FOR LIVING ORGANISM

TECHNICAL FIELD

The present invention relates to an apparatus for supplying high-concentration hydrogen gas for a living organism.

BACKGROUND ART

There is known an apparatus for supplying high-concentration hydrogen gas for a living organism configured such that an air mixer is attached to a part of a conduit pipe from a hydrogen gas generator to a nasal cavity cannula and the concentration of hydrogen gas to be supplied can be arbitrarily set (Patent Document 1).

PRIOR ART DOCUMENT

Patent Document

[Patent Document 1] JP 2009-5881 A

SUMMARY OF INVENTION

Problems to be Solved by Invention

According to the above conventional apparatus for supplying high-concentration hydrogen gas for a living organism, however, hydrogen gas of a concentration exceeding the explosion limit passes through the conduit pipe from the hydrogen gas generator to the air mixer because the air mixer is attached to a part of the conduit pipe to the nasal cavity cannula to mix air with the generated hydrogen gas. Therefore, the apparatus cannot be used safely in medical practice or at home.

Problems to be solved by the present invention include providing an apparatus for supplying high-concentration hydrogen gas for a living organism by which hydrogen gas having health benefits can be used safely in medical practice or at home.

Means for Solving Problems

The present invention solves the above problems by providing an apparatus for supplying high-concentration hydrogen gas thr a living organism. The apparatus is configured to blow diluent gas to a cathode surface at which hydrogen gas is generated or to a cathode water surface. The apparatus can thereby maintain the hydrogen gas concentration at lower than 18.3 vol %, which is the lower limit of detonation, or at lower than 4 vol %, which is the lower limit of explosion, at any time from a time when the hydrogen gas is generated to a time when the hydrogen gas is supplied to a living organism.

Effect of Invention

According to the present invention, hydrogen gas having health benefits can be used safely in medical practice or at home.

BRIEF DESCRIPTION OF DRAWING(S)

FIG. 1 is a block diagram illustrating an apparatus for supplying high-concentration hydrogen gas for a living organism according to an embodiment of the present invention.

MODE(S) FOR CARRYING OUT THE INVENTION

As shown in FIG. 1, an apparatus 1 for supplying high-concentration hydrogen gas for a living organism according to an embodiment of the present invention comprises: an electrolytic cell 1; a direct-current power source 2 that applies a direct-current voltage to electrode plates 14 and 15 in the electrolytic cell 1; and a diluent gas supplier 3 for diluting hydrogen gas generated from the electrode plate 14 or 15 that is to be a cathode. The electrolytic cell 1 has: an electrolytic chamber 11 to which subject raw water 12 is introduced; at least one membrane 13 that separates inside and outside of the electrolytic chamber 11; and at least one pair of electrode plates 14 and 15 provided respectively in the inside and the outside of the electrolytic chamber 11 so as to sandwich the membrane 13. The electrode plate 15 located outside the electrolytic chamber 11 is provided to be in contact with the membrane 13. The diluent gas supplied from the diluent gas supplier 3 is blown to the vicinity of the electrode plate 14 or 15, which is to be the cathode, thereby to constantly maintain a hydrogen gas concentration in the vicinity of the cathode during electrolysis at lower than 18.3 vol %, which is the lower limit of detonation, or at lower than 4 vol %, which is the lower limit of explosion, so that mixed gas comprising the hydrogen gas and the diluent gas is supplied to a living organism.

Here, the apparatus 1 for supplying high-concentration hydrogen gas for a living organism is to supply hydrogen gas to a living organism mainly for the purpose of health maintenance and/or functional maintenance of living organisms (including cells and organs), disease improvement and/or functional improvement, or health check and/or functional measurement. Examples of the supply means thereof may include, but are not limited to, supply by way of inhalation from the nasal cavity and/or mouth cavity, supply by way of exposure of and/or blowing to the skin or organ, supply by way of exposure of and/or blowing to living organism applicable liquid, such as liquid drug and organ storage liquid, which is assumed to be applied to a living organism, and supply by way of diffusion from the outside of a container or circuit which is provided with a living organism.

The subject raw water as used herein is water that can generate hydrogen gas at the cathode through a process of electrolysis of the water, and examples thereof include tap water, clean water, purified water, distilled water and the like. The subject raw water may appropriately contain electrolytes, such as calcium ion and magnesium ion. Examples of the electrolytic cell 1 include an electrolytic cell as described in U.S. Pat. No. 3,349,710, etc, for example. Again, the electrolytic cell 1 has at least one membrane 13 that separates the inside and the outside of the electrolytic chamber 11 and at least one pair of electrode plates 14 and 15 provided respectively in the inside and the outside of the electrolytic chamber 11 so as to sandwich the membrane 13. The electrode plate 15 located outside the electrolytic chamber 11 is provided to be in contact with the membrane 13.

The electrode plate 14 located inside the electrolytic chamber 11 may be provided to be in contact with the membrane 13, or may also be provided to leave a narrow space from the membrane (for example 1 cm or less, preferably 5 mm or less, more preferably 1 mm or less, and further preferably 0.5 mm or less from the membrane).

Examples of the electrode plates 14 and 15 to be used include, but are not limited to, those using titanium plates as base materials on which noble metal selected from the group of platinum, iridium, palladium and the like is plated.

It is preferable that a cation exchange membrane is used as the membrane 13. In consideration of necessary factors such as the ion conductivity, physical strength, gas barrier property, chemical stability, electrochemical stability and thermal stability, there may preferably be used an all fluorine-based sulfonic acid membrane that comprises a sulfonic group as the electrolyte group. Examples of such a membrane include a membrane of Nafion (registered trademark, a DuPont product) which is a copolymer membrane of tetrafluoroethylene and perfluorovinyl ether having a sulfonic group, a membrane of Flemion (registered trademark, available from ASAHI GLASS CO., LTD.) and a membrane of Aciplex (registered trademark, available from Asahi Kasei Corporation).

If the membrane 13 is absent between the electrode plates 14 and 15, the hydrogen gas generated from the cathode is mixed with oxygen gas and/or chlorine gas generated from the anode. Thus, such a configuration is not preferable in view of the risk of explosion and the toxicity to a living organism.

It is known in particular that hydrogen gas and chlorine gas react together at ordinary temperature in response to light. Therefore, in the mixed gas comprising the hydrogen gas and the diluent gas according to the present invention, the lower the chlorine gas concentration is, the more desirable it is. More specifically, the chlorine gas concentration is preferably 1 ppm or less, more preferably 0.5 ppm or less, and further preferably 0.1 ppm or less.

By introducing the subject raw water 12 into the inside of the electrolytic chamber 11 and applying a direct-current voltage from the direct-current power source 2, the subject raw water 12 is electrolyzed to generate hydrogen gas at the cathode. Two cases are possible here, i.e., a case in which the electrode plate 14 located inside the electrolytic chamber 11 is used as the cathode while the electrode plate 15 located outside the electrolytic chamber 11 is used as the anode, and a case in which the electrode plate 14 located inside the electrolytic chamber 11 is used as the anode while the electrode plate 15 located outside the electrolytic chamber 11 is used as the cathode. These cases will be described below.

At first, when the electrode plate 14 located inside the electrolytic chamber 11 is used as the cathode while the electrode plate 15 located outside the electrolytic chamber 11 is used as the anode, the hydrogen gas generated from the cathode by electrolysis transfers to a headspace 4 (a space above the cathode water surface) located inside the electrolytic chamber 11 while moving upward in the water (cathode water) in the electrolytic chamber 11. Here, if the electrolytic chamber 11 is closed such as by a cover to avoid diffusion of the hydrogen gas into the air, the hydrogen concentration in the headspace 4 increases as time passes and will exceed 18.3 vol %, which is the lower limit of detonation of the hydrogen gas, or 4 vol %, which is the lower limit of explosion. On the other hand, even if the electrolytic chamber 11 is not closed and the headspace 4 is opened to the air, some spot in the vicinity of the cathode water surface will be formed, even in a local manner, with a concentration range of 18.5 vol % or more and 59 vol % or less, i.e., a concentration range of hydrogen within which detonation occurs, or with a concentration range of 4 vol % or more and 75 vol % or less, i.e., a concentration range of hydrogen within which explosion occurs. In fact, according to the applicants' knowledge, when flame is moved to approach the cathode water surface at the time of electrolysis, small detonating sound sometimes occurs somewhere in the approaching process, not only in a case of the present invention but in other cases.

It is said in general that hydrogen reacts with oxygen in the air to become detonating gas when the hydrogen concentration exceeds 4 vol %. However, under a condition of blowing the diluent gas as in the present invention at a constant flowing volume, an event that such detonating gas leads to actual ignition (deflagration) may occur in most situations at a concentration much higher than 4 vol % which is said to be the explosion limit of hydrogen. In fact, as long as the electrolysis is carried on, the hydrogen is generated constantly from the cathode or the cathode water surface, but even if flame is moved to approach the cathode or the cathode water surface in a hydrogen concentration of 4 vol %, the detonating sound may not be audible, or may be with a considerably small sound if audible. According to the applicants' experiment, when the hydrogen concentration exceeds 10 to 15 vol % (lower limit of deflagration), the detonating sound is offensive to the ear to some extent and small deflagration occurs.

On the other hand, even though a high concentration of hydrogen is intended to be obtained, it may be inappropriate to require a concentration of hydrogen higher than 18.3% (lower limit of detonation), i.e., a concentration at which the reaction of hydrogen and oxygen causes a shock wave as detonation to propagate around there.

Under such recognition, the applicants have developed an apparatus for supplying high-concentration hydrogen gas for a living organism which can safely supply hydrogen gas of a high concentration higher than 4 vol % which is conventionally said to be the explosion limit.

That is, according to the present invention, the hydrogen gas concentration at the cathode or the cathode water surface during electrolysis may be maintained at lower than 18.3 vol %, more preferably lower than 15 vol %, and most preferably lower than 4 vol %.

Next, when the electrode plate 14 located inside the electrolytic chamber 11 is used as the anode while the electrode plate 15 located outside the electrolytic chamber 11 is used as the cathode, the cathode is located outside the electrolytic chamber 11 and thus basically in a state of being opened to the air. In this case, like the above, some spot in the vicinity of the exposed cathode will be formed, even in a local manner, with a concentration range of 18.5 vol % or more and 59 vol % or less, i.e., a concentration range of hydrogen within which detonation occurs, or with a concentration range of 4 vol % or more and 75 vol % or less, i.e., a concentration range of hydrogen within which explosion occurs. In addition, different from the case in which the electrode plate 14 located inside the electrolytic chamber 11 is used as the cathode, the possibility of explosion due to unexpected ignition may increase because water for absorbing heat is not present around there unless a side chamber 16 as will be described later is provided to be filled with water.

Therefore, regardless of whether the case in which the electrode plate 14 located inside the electrolytic chamber 11 is used as the cathode while the electrode plate 15 located outside the electrolytic chamber 11 is used as the anode or the case in which the electrode plate 14 located inside the electrolytic chamber 11 is used as the anode while the electrode plate 15 located outside the electrolytic chamber 11 is used as the cathode, it is important in the present invention to strictly control the hydrogen gas concentration in the vicinity of the cathode during electrolysis through blowing the diluent gas to the vicinity of the cathode from the diluent gas supplier 3.

That is, in a phase of "the cathode during electrolysis" in which hydrogen of the highest concentration is generated according to the present invention, it is important to immediately dilute the generated hydrogen gas thereby to maintain the hydrogen gas concentration at lower than 18.3 vol % or lower than 4 vol % through all the flowing pass of the hydrogen gas from the generation to the supply to a living organism. Therefore, it is preferable that the supply of the diluent gas is operated at the same time when the electrolysis is initiated or operated in advance thereof. It is also preferable to provide a mechanism that can automatically stop the electrolysis when the diluent gas supplier 3 stops due to unexpected trouble. In view of the above, the present invention may exclude an embodiment configured to discharge the hydrogen gas generated at the cathode from the electrolytic chamber 11 and thereafter dilute the hydrogen gas using an air mixer provided at any location along the conduit pipe.

Note that the diluent gas as used in the present invention refers to a concept that includes normal air and artificial air as well as medical gas of which the oxygen concentration is adjusted and other medical gases which contain other components. Examples of the diluent gas supplier 3, which supplies such diluent gas, include an apparatus that can blow the diluent gas, such as an air pump.

The vicinity of the cathode as used herein includes a concept of the vicinity of the cathode water surface if water is present around there, as described above. The vicinity refers to a concept that includes a position separated by 7 cm, preferably 5 cm, more preferably 3 cm, and most preferably 1 cm, from the cathode (or the cathode water surface). According to the present invention, the hydrogen gas concentration in the vicinity of the cathode is measured at each of a time when 1 minute has elapsed after starting the electrolysis, a time when half an estimated electrolysis time has passed, and a time when the electrolysis has been completed. If the hydrogen gas concentration is lower than 4 vol % at each of the times, it is deemed that "the hydrogen gas concentration in the vicinity of the cathode during electrolysis is constantly maintained at lower than 4 vol %." If the hydrogen gas concentration is lower than 18.3 vol % at each of the times, it is deemed that "the hydrogen gas concentration in the vicinity of the cathode during electrolysis is constantly maintained at lower than 18.3 vol %."

The present invention is an invention that relates consistently to an apparatus for supplying high-concentration hydrogen gas for a living organism. Therefore, even though the hydrogen gas concentration is to be maintained lower than 18.3 vol % or lower than 4 vol %, the dilution may not have to be needed beyond necessity. It is thus preferable that the present invention is associated with management of the electrolytic condition and/or management of the flow volume rather than blindly blowing the diluent gas into the electrolytic cell for the purpose of reducing the hydrogen gas concentration close to zero without limit so that the hydrogen gas generated from the cathode can be safely discarded outside the system.

More specifically, in terms of the amount of air or high-concentration oxygen gas which human beings or animals inhale for 1 minute, for example, when the diluent gas is blown at a flow volume of 2 L/min or more, preferably 4 L/min or more, more preferably 6 L/min or more, further preferably 8 L/min or more, and particularly preferably 10 L/min or more, for example, it is preferable that the electrolytic condition is managed such that the hydrogen gas concentration in the mixed gas comprising the hydrogen gas and the diluent gas is 0.1 vol % or more, preferably 03 vol % or more, more preferably 0.5 vol % or more, further preferably 1 vol % or more, and most preferably 2.5 vol % or more, and less than 4 vol %. In an alternative embodiment, when the diluent gas is blown at a flow volume of 0.5 L/min or more, preferably 1 L/min or more, more preferably 2 L/min or more, further preferably 4 L/min or more, and particularly preferably 6 L/min or more, for example, it is preferable that the electrolytic condition is managed such that the hydrogen gas concentration in the mixed gas comprising the hydrogen gas and the diluent gas is 0.5 vol % or more, preferably 1 vol % or more, more preferably 2 vol % or more, and further preferably 4 vol % or more (or a concentration that exceeds 4 vol %), and less than 18.3 vol % and preferably less than 15 vol %.

Such an electrolytic condition is associated with the volume of the subject raw water, the water temperature of the subject raw water, the electrolytic current value and the like. For example, when the diluent gas is blown to the vicinity of the cathode at a flow volume of 5 L/min for the electrolytic chamber 11 having 1.4 L of the subject raw water 12, if the subject raw water 12 is electrolyzed with an electrolytic current of 15 A, the hydrogen gas concentration in the mixed gas comprising the hydrogen gas and the diluent gas is maintained at around 2.4 vol % at each of a time when 1 minute has elapsed after starting the electrolysis, a time when half an estimated electrolysis time has passed, and a time when the electrolysis has been completed. Here, as the electrolysis time is elongated, the water temperature of the subject raw water 12 in the electrolytic chamber 11 increases. In order to prevent the increase in water temperature of the subject raw water 12 while maintaining the hydrogen gas concentration in the mixed gas, any appropriate adjustment may be possible without changing the electrolytic current value, such as by decreasing the water volume of the subject raw water 12 (volume of the electrolytic chamber 11), decreasing the water temperature of the subject raw water 12, and increasing the surface area of the electrode plates 14 and 15.

When the electrode plate 14 located inside the electrolytic chamber 11 is used as the anode while the electrode plate 15 located outside the electrolytic chamber 11 is used as the cathode, the electrolysis may be performed by enclosing the electrode plate 15 located outside the electrolytic chamber 11 in a side chamber 16 and filling not only the electrolytic chamber 11 but the side chamber 16 with the subject raw water. This allows to suppress the increase in water temperature of the subject raw water 12 while maintaining the hydrogen gas concentration in the mixed gas. In general, the side chamber 16 comprises six surfaces, i.e., a first surface that includes the electrode plate 15 located outside the electrolytic chamber 11; four surfaces that extend horizontally from the first surface so as to have four sides in contact with the first surface; and a second surface that is placed to face the first surface, but is not limited thereto. The side chamber 16 can be used as a space that separates the obtained mixed gas from the external air even when the side chamber 16 is not filled with the subject raw water. However, even though the mixed gas according to the present invention does not contain 18.3 vol % or more or 4 vol % or more of hydrogen gas, it may not necessarily be desirable to store gas that contains hydrogen gas beyond necessity. Therefore, the volume of the side chamber 16 may be, but is not limited to, three times or less the volume of the electrolytic chamber 11, preferably twice or less, more preferably the same or less, and further preferably 0.5 times or less.

Examples of a form to supply the mixed gas to a living organism include a form to inhale the mixed gas by moving the face directly to the vicinity of the cathode or cathode water surface or to the cathode chamber and a form to inhale the mixed gas from a mixed gas outlet 18 provided at the electrolytic chamber 11 or at the side chamber 16.

The present invention also encompasses various embodiments, such as an apparatus for supplying high-concentration hydrogen gas for a living organism configured such that: the electrolytic chamber 11 is provided with a diluent gas inlet 17a that introduces the diluent gas from the diluent gas supplier 3 and a mixed gas outlet 18a that discharges the mixed gas; and, in a state in which the subject raw water 12 is introduced into the electrolytic chamber 11, the direct-current power source 2 applies a direct-current voltage to both the electrode plates 14 and 15 using the electrode plate 14 provided inside the electrolytic chamber 11 as the cathode and the electrode plate 15 provided outside the electrolytic chamber 11 as the anode, and an apparatus for supplying high-concentration hydrogen gas for a living organism configured such that: the side chamber 16 is provided with a diluent gas inlet 17 that introduces the diluent gas from the diluent gas supplier 3 and a mixed gas outlet 18 that discharges the mixed gas; and, in a state in which the subject raw water 12 is introduced into the inside of the electrolytic chamber 11, the direct-current power source 2 applies a direct-current voltage to both the electrode plates 14 and 15 using the electrode plate 14 provided inside the electrolytic chamber 11 as the anode and the electrode plate 15 provided outside the electrolytic chamber 11 as the cathode.

In order to provide a reversible feature that the electrode plates 14 and 15 can be used even when the polarities are reversed, the diluent gas inlet 17 and the mixed gas outlet 18 may be provided at each of the electrolytic chamber 11 and the side chamber 16.

In the above embodiments, an attachment such as a nasal cavity cannula may be appropriately connected to the mixed gas outlet 18 or 18a thereby to enhance the convenience at the time of supply to a living organism and/or the stability of supply of the mixed gas.

EXAMPLES

Working examples of the present invention will hereinafter be described. Unless otherwise stated in the present application, various meters used to measure various physical property values are a hydrogen gas concentration meter "XP-3140 (available from New Cosmos Electric Co., Ltd.)", an ammeter "CLAMP ON AC/DC HiTESTER 3265 (available from HIOKI E.E. CORPORATION)", and a voltmeter "CDM-2000 (available from CUSTOM corporation)."

Example 1

An electrolytic cell has been prepared to have an electrolytic chamber to which subject raw water is introduced, a cation exchange membrane ("Nafion 424" (a DuPont product)) that separates inside and outside of the electrolytic chamber, and a pair of platinum electrodes provided in the inside and the outside of the electrolytic chamber so as to sandwich the cation exchange membrane, wherein the electrode plate located outside the electrolytic chamber is provided to be in contact with the cation exchange membrane, and the electrode plate located inside the electrolytic chamber is also provided to be in contact with the cation exchange membrane. The electrolytic chamber was filled with 1.4 L of Fujisawa city tap water of a water temperature of 20.8° C., and the cation exchange membrane was also wet with the water.

Thereafter, electrolysis was performed with an electrolytic current of 15 A by applying a direct-current voltage from a direct-current power source to both of the electrodes using the electrode plate located inside the electrolytic chamber as the cathode while using the electrode plate located outside the electrolytic chamber as the anode.

Concurrently with the start of electrolysis, normal air was blown at 5 L/min to the cathode (or the cathode water surface) from an air pump (Silent β 120 (available from MARUKAN. Co., Ltd.)) as the diluent gas supplier. The hydrogen gas concentration at a position separated by 7 cm from the cathode water surface, the electrolytic voltage, and the water temperature in the electrolytic chamber, were measured at a time when 1 minute elapsed after the start of electrolysis, at a time when 5 minutes elapsed after the start of electrolysis, and at a time when the electrolysis was completed (when 10 minutes elapsed after the start of electrolysis). Results thereof are listed in Table 1.

Example 2

The electrolytic chamber in Example 1 was provided further with a side chamber enclosing the electrode plate located outside the electrolytic chamber, and each of the electrolytic chamber and the side chamber was filled with 1.4 L of Fujisawa city tap water of a water temperature of 19.0° C. Thereafter, electrolysis was performed with an electrolytic current of 15 A by applying a direct-current voltage from the direct-current power source to both of the electrodes using the electrode plate located inside the electrolytic chamber as the cathode while using the electrode plate located outside the electrolytic chamber as the anode.

Concurrently with the start of electrolysis, normal air was blown at 5 L/min to the cathode (or the cathode water surface) from the above-described air pump as the diluent gas supplier. The hydrogen gas concentration at a position separated by 7 cm from the cathode water surface, the electrolytic voltage, and the water temperature in the electrolytic chamber, were measured at a time when 1 minute elapsed after the start of electrolysis, at a time when 5 minutes elapsed after the start of electrolysis, and at a time when the electrolysis was completed (when 10 minutes elapsed after the start of electrolysis). Results thereof are listed in Table 1.

Example 3

An electrolytic cell has been prepared to be characterized in having an electrolytic chamber to which subject raw water is introduced, the above-described cation exchange membrane that separates inside and outside of the electrolytic chamber, and a pair of platinum electrodes provided in the inside and the outside of the electrolytic chamber so as to sandwich the cation exchange membrane, wherein the electrode plate located outside the electrolytic chamber is provided to be in contact with the cation exchange membrane, and the electrode plate located inside the electrolytic chamber is also provided to be in contact with the cation exchange membrane. The electrolytic chamber was filled with 1.4 L of Fujisawa city tap' water of a water temperature of 20.1° C., and electrolysis was performed with an electrolytic current of 15 A by applying a direct-current voltage from the direct-current power source to both of the electrodes using the electrode plate located inside the electrolytic chamber as the anode while using the electrode plate located outside the electrolytic chamber as the cathode.

Concurrently with the start of electrolysis, normal air was blown at 5 L/min to the cathode from the above-described air pump as the diluent gas supplier. The hydrogen gas concentration at a position separated by 7 cm from the cathode, the electrolytic voltage, and the water temperature in the electrolytic chamber, were measured at a time when 1 minute elapsed after the start of electrolysis, at a time when 5 minutes elapsed after the start of electrolysis, and at a time when the electrolysis was completed (when 10 minutes elapsed after the start of electrolysis). Results thereof are listed in Table 1.

Comparative Examples 1 to 3

Without blowing normal air in Examples 1 to 3, the hydrogen gas concentration at a position separated by 7 cm from the cathode water surface or the cathode, the electrolytic voltage, and the water temperature in the electrolytic chamber, were measured at a time when 1 minute elapsed after the start of electrolysis, at a time when 5 minutes elapsed after the start of electrolysis, and at a time when the electrolysis was completed (when 10 minutes elapsed after the start of electrolysis). Results thereof are listed in Table 1. Note that the water temperatures of the subject raw water used in Comparative Examples 1 to 3 were 20.1° C., 20.9° C., and 20.8° C., respectively.

TABLE 1

|  |  | After 1 minute | After 5 minutes | After 10 minutes |
|---|---|---|---|---|
| Example 1 | Hydrogen gas concentration (%) | 2.2 | 2.4 | 2.3 |
|  | Electrolytic voltage (V) | 14.5 | 14.2 | 14.1 |
|  | Water temperature in electrolytic chamber (° C.) |  |  | 41.5 |
| Comparative Example 1 | Hydrogen gas concentration (%) | 4.1 | 21.0 | 32.0 |
|  | Electrolytic voltage (V) | 14.9 | 14.6 | 15.0 |
|  | Water temperature in electrolytic chamber (° C.) |  |  | 39.8 |
| Example 2 | Hydrogen gas concentration (%) | 2.3 | 2.4 | 2.4 |
|  | Electrolytic voltage (V) | 11.2 | 11.5 | 11.5 |
|  | Water temperature in electrolytic chamber (° C.) |  |  | 28.4 |
| Comparative Example 2 | Hydrogen gas concentration (%) | 4.2 | 22.0 | 34.0 |
|  | Electrolytic voltage (V) | 13.5 | 13.5 | 13.0 |
|  | Water temperature (° C.) in electrolytic chamber (° C.) |  |  | 31.2 |
| Example 3 | Hydrogen gas concentration (%) | 2.4 | 2.4 | 2.4 |
|  | Electrolytic voltage (V) | 10.8 | 10.6 | 10.6 |
|  | Water temperature in electrolytic chamber (° C.) | 21.0 | 26.1 | 31.3 |
| Comparative Example 3 | Hydrogen gas concentration (%) | 3.2 | 15.0 | 26.0 |
|  | Electrolytic voltage (V) | 11.7 | 11.4 | 10.6 |
|  | Water temperature in electrolytic chamber (° C.) | 21.9 | 27.2 | 33.2 |

Example 4

An electrolytic cell has been prepared to have an electrolytic chamber to which subject raw water is introduced, a cation exchange membrane ("Nafion 424" (a DuPont product)) that separates inside and outside of the electrolytic chamber, and a pair of platinum electrodes provided in the inside and the outside of the electrolytic chamber so as to sandwich the cation exchange membrane, wherein the electrode plate located outside the electrolytic chamber is provided to be in contact with the cation exchange membrane, and the electrode plate located inside the electrolytic chamber is also provided to be in contact with the cation exchange membrane. The electrolytic chamber was filled with 1.4 L of Fujisawa city tap water of a water temperature of 20.8° C., and the cation exchange membrane was also wet with the water.

Thereafter, electrolysis was performed with an electrolytic current of 21 A by applying a direct-current voltage from a direct-current power source to both of the electrodes using the electrode plate located inside the electrolytic chamber as the cathode while using the electrode plate located outside the electrolytic chamber as the anode.

Concurrently with the start of electrolysis, normal air was blown at 1 L/min to the cathode (or the cathode water surface) from an air pump (Silent β 120 (available from MARUKAN. Co., Ltd.)) as the diluent gas supplier. The hydrogen gas concentration at a position separated by 7 cm from the cathode water surface, the electrolytic voltage, and the water temperature in the electrolytic chamber, were measured at a time when 1 minute elapsed after the start of electrolysis, at a time when 5 minutes elapsed after the start of electrolysis, and at a time when the electrolysis was completed (when 10 minutes elapsed after the start of electrolysis). Results thereof are listed in Table 2.

Example 5

The electrolytic chamber in Example 4 was provided further with a side chamber enclosing the electrode plate located outside the electrolytic chamber, and each of the electrolytic chamber and the side chamber was filled with 1.4 L of Fujisawa city tap water of a water temperature of 26.5° C. Thereafter, electrolysis was performed with an electrolytic current of 21 A by applying a direct-current voltage from the direct-current power source to both of the electrodes using the electrode plate located inside the electrolytic chamber as the cathode while using the electrode plate located outside the electrolytic chamber as the anode.

Concurrently with the start of electrolysis, normal air was blown at 1 L/min to the cathode (or the cathode water surface) from the above-described air pump as the diluent gas supplier. The hydrogen gas concentration at a position separated by 7 cm from the cathode water surface, the electrolytic voltage, and the water temperature in the electrolytic chamber, were measured at a time when 1 minute elapsed after the start of electrolysis, at a time when 5 minutes elapsed after the start of electrolysis, and at a time when the electrolysis was completed (when 10 minutes elapsed after the start of electrolysis). Results thereof are listed in Table 2.

Example 6

An electrolytic cell has been prepared to be characterized in having an electrolytic chamber to which subject raw water is introduced, the above-described cation exchange membrane that separates inside and outside of the electrolytic chamber, and a pair of platinum electrodes provided in the inside and the outside of the electrolytic chamber so as to sandwich the cation exchange membrane, wherein the electrode plate located outside the electrolytic chamber is provided to be in contact with the cation exchange membrane, and the electrode plate located inside the electrolytic chamber is also provided to be in contact with the cation exchange membrane. The electrolytic chamber was filled with 1.4 L of Fujisawa city tap water of a water temperature of 25.9° C., and electrolysis was performed with an electrolytic current of 21 A by applying a direct-current voltage from the direct-current power source to both of the electrodes using the electrode plate located inside the electrolytic chamber as the anode while using the electrode plate located outside the electrolytic chamber as the cathode.

Concurrently with the start of electrolysis, normal air was blown at 1 L/min to the cathode from the above-described air pump as the diluent gas supplier. The hydrogen gas concentration at a position separated by 7 cm from the cathode, the electrolytic voltage, and the water temperature in the electrolytic chamber, were measured at a time when 1 minute elapsed after the start of electrolysis, at a time when 5 minutes elapsed after the start of electrolysis, and at a time when the electrolysis was completed (when 10 minutes elapsed after the start of electrolysis). Results thereof are listed in Table 2.

Comparative Examples 4 to 6

Without blowing normal air in Examples 4 to 6, the hydrogen gas concentration at a position separated by 7 cm from the cathode water surface or the cathode, the electrolytic voltage, and the water temperature in the electrolytic chamber, were measured at a time when 1 minute elapsed after the start of electrolysis, at a time when 5 minutes elapsed after the start of electrolysis, and at a time when the electrolysis was completed (when 10 minutes elapsed after the start of electrolysis). Results thereof are listed in Table 2. Note that the water temperatures of the subject raw water used in Comparative Examples 4 to 6 were 20.1° C., 20.8° C., and 26.2° C., respectively.

TABLE 2

|  |  | After 1 minute | After 5 minute | After 10 minutes |
|---|---|---|---|---|
| Example 4 | Hydrogen gas concentration (%) | 5.4 | 13 | 14 |
|  | Electrolytic voltage (V) | 18.1 | 17.2 | 16.7 |
|  | Water temperature in electrolytic chamber (° C.) |  |  | 50.2 |
| Comparative Example 4 | Hydrogen gas concentration (%) | 5.6 | 32 | 49 |
|  | Electrolytic voltage (V) | 17.4 | 17.2 | 17.1 |
|  | Water temperature in electrolytic chamber (° C.) |  |  | 39.8 |
| Example 5 | Hydrogen gas concentration (%) | 5.5 | 13 | 14 |
|  | Electrolytic voltage (V) | 15.7 | 15.0 | 14.3 |
|  | Water temperature in electrolytic chamber (° C.) |  |  | 41.1 |
| Comparative Example 5 | Hydrogen gas concentration (%) | 6.2 | 31 | 47 |
|  | Electrolytic voltage (V) | 16.9 | 16.1 | 15.3 |
|  | Water temperature in electrolytic chamber (° C.) |  |  | 42.5 |
| Example 6 | Hydrogen gas concentration (%) | 3.7 | 12 | 14 |
|  | Electrolytic voltage (V) | 12.1 | 12.2 | 12.2 |
|  | Water temperature in electrolytic chamber (° C.) | 27.4 | 36.1 | 44.7 |
| Comparative Example 6 | Hydrogen gas concentration (%) | 5.1 | 24 | 42 |
|  | Electrolytic voltage (V) | 13.4 | 13.1 | 13.2 |
|  | Water temperature in electrolytic chamber (° C.) | 27.8 | 35.9 | 46.0 |

Example 7

An electrolytic cell has been prepared to have an electrolytic chamber to which subject raw water is introduced, a cation exchange membrane ("Nafion 424" (a DuPont product)) that separates inside and outside of the electrolytic chamber, and a pair of platinum electrodes provided in the inside and the outside of the electrolytic chamber so as to sandwich the cation exchange membrane, wherein the electrode plate located outside the electrolytic chamber is provided to be in contact with the cation exchange membrane, and the electrode plate located inside the electrolytic chamber is also provided to be in contact with the cation exchange membrane. The electrolytic chamber was filled with 1.4 L of Fujisawa city tap water of a water temperature of 25.8° C., and the cation exchange membrane was also wet with the water.

Thereafter, electrolysis was performed with an electrolytic current of 27 A by applying a direct-current voltage from a direct-current power source to both of the electrodes using the electrode plate located inside the electrolytic chamber as the cathode while using the electrode plate located outside the electrolytic chamber as the anode.

Concurrently with the start of electrolysis, normal air was blown at 1 L/min to the cathode (or the cathode water surface) from an air pump (Silent β 120 (available from MARUKAN, Co., Ltd.)) as the diluent gas supplier. The hydrogen gas concentration at a position separated by 7 cm from the cathode water surface, the electrolytic voltage, and the water temperature in the electrolytic chamber, were measured at a time when 1 minute elapsed after the start of electrolysis, at a time when 5 minutes elapsed after the start of electrolysis, and at a time when the electrolysis was completed (when 10 minutes elapsed after the start of electrolysis). Results thereof are listed in Table 3.

Example 8

The electrolytic chamber in Example 7 was provided further with a side chamber enclosing the electrode plate located outside the electrolytic chamber, and each of the electrolytic chamber and the side chamber was filled with 1.4 L of Fujisawa city tap water of a water temperature of 26.3° C. Thereafter, electrolysis was performed with an electrolytic current of 27 A by applying a direct-current voltage from the direct-current power source to both of the electrodes using the electrode plate located inside the electrolytic chamber as the cathode while using the electrode plate located outside the electrolytic chamber as the anode.

Concurrently with the start of electrolysis, normal air was blown at 1 L/min to the cathode (or the cathode water surface) from the above-described air pump as the diluent gas supplier. The hydrogen gas concentration at a position separated by 7 cm from the cathode water surface, the electrolytic voltage, and the water temperature in the electrolytic chamber, were measured at a time when 1 minute elapsed after the start of electrolysis, at a time when 5 minutes elapsed after the start of electrolysis, and at a time when the electrolysis was completed (when 10 minutes elapsed after the start of electrolysis). Results thereof are listed in Table 3.

Example 9

An electrolytic cell has been prepared to be characterized in having an electrolytic chamber to which subject raw water is introduced, the above-described cation exchange membrane that separates inside and outside of the electrolytic chamber, and a pair of platinum electrodes provided in the inside and the outside of the electrolytic chamber so as to sandwich the cation exchange membrane, wherein the electrode plate located outside the electrolytic chamber is provided to be in contact with the cation exchange membrane, and the electrode plate located inside the electrolytic chamber is also provided to be in contact with the cation exchange membrane. The electrolytic chamber was filled with 1.4 L of Fujisawa city tap water of a water temperature of 25.8° C., and electrolysis was performed with an electrolytic current of 27 A by applying a direct-current voltage from the direct-current power source to both of the electrodes using the electrode plate located inside the electrolytic chamber as the anode while using the electrode plate located outside the electrolytic chamber as the cathode.

Concurrently with the start of electrolysis, normal air was blown at 1 L/min to the cathode from the above-described air pump as the diluent gas supplier. The hydrogen gas concentration at a position separated by 7 cm from the cathode, the electrolytic voltage, and the water temperature in the electrolytic chamber, were measured at a time when 1 minute elapsed after the start of electrolysis, at a time when 5 minutes elapsed after the start of electrolysis, and at a time when the electrolysis was completed (when 10 minutes elapsed after the start of electrolysis). Results thereof are listed in Table 3.

Comparative Examples 7 to 9

Without blowing normal air in Examples 7 to 9, the hydrogen gas concentration at a position separated by 7 cm from the cathode water surface or the cathode, the electrolytic voltage, and the water temperature in the electrolytic chamber, were measured at a time when 1 minute elapsed after the start of electrolysis, a time when 5 minutes elapsed after the start of electrolysis, and a time when the electrolysis was completed (when 10 minutes elapsed after the start of electrolysis). Results thereof are listed in Table 3. Note that the water temperatures of the subject raw water used in Comparative Examples 7 to 9 were 25.9° C., 26.8° C., and 25.9° C., respectively.

TABLE 3

| | | After 1 minute | After 5 minutes | After 10 minutes |
|---|---|---|---|---|
| Example 7 | Hydrogen gas concentration (%) | 6.4 | 16 | 18 |
| | Electrolytic voltage (V) | 21.9 | 18.4 | 18.2 |
| | Water temperature in electrolytic chamber (° C.) | | | 58.4 |
| Comparative Example 7 | Hydrogen gas concentration (%) | 8.3 | 38 | 62 |
| | Electrolytic voltage (V) | 22.7 | 21.3 | 20.6 |
| | Water temperature in electrolytic chamber (° C.) | | | 61.2 |
| Example 8 | Hydrogen gas concentration (%) | 6.9 | 17 | 18 |
| | Electrolytic voltage (V) | 21.0 | 19.4 | 18.1 |
| | Water temperature in electrolytic chamber (° C.) | | | 45.2 |
| Comparative Example 8 | Hydrogen gas concentration (%) | 8.4 | 38 | 59 |
| | Electrolytic voltage (V) | 19.7 | 18.5 | 17.2 |
| | Water temperature in electrolytic chamber (° C.) | | | 46.7 |
| Example 8 | Hydrogen gas concentration (%) | 5.0 | 15 | 18 |
| | Electrolytic voltage (V) | 14.9 | 13.0 | 13.2 |
| | Water temperature in electrolytic chamber (° C.) | 28.5 | 38.8 | 50.4 |
| Comparative Example 9 | Hydrogen gas concentration (%) | 6.5 | 29 | 52 |
| | Electrolytic voltage (V) | 13.4 | 13.6 | 13.4 |
| | Water temperature in electrolytic chamber (° C.) | 28.8 | 39.7 | 52.7 |

DESCRIPTION OF REFERENCE NUMERALS

1 . . . Apparatus for supplying high-concentration hydrogen gas for a living organism
11 . . . Electrolytic chamber
12 . . . Subject raw water
13 . . . Membrane
14, 15 . . . Electrode plate
16 . . . Side chamber
17, 17a . . . Diluent gas inlet
18, 18a . . . Mixed gas outlet
2 . . . Direct-current power source
3 . . . Diluent gas supplier
4 . . . Headspace

The invention claimed is:
1. An apparatus for supplying high-concentration hydrogen gas for a living organism, the apparatus comprising:
an electrolytic cell having an electrolytic chamber to which subject raw water is introduced, at least one membrane that separates inside and outside of the electrolytic chamber, and at least one pair of electrode plates provided in the inside and the outside of the electrolytic chamber so as to sandwich the membrane, one electrode plate in the outside of the electrolytic chamber being provided to be in contact with the membrane;
a direct-current power source that applies a direct-current voltage to the pair of electrode plates; and
a diluent gas supplier for diluting hydrogen gas generated from a cathode electrode plate of the electrode plates, wherein the apparatus blows diluent gas supplied from the diluent gas supplier to the cathode electrode plate thereby to constantly maintain a hydrogen gas concentration measured at a position separated by 7 cm from the cathode electrode plate during electrolysis at lower than 18.3 vol % so that mixed gas comprising the hydrogen gas and the diluent gas and having a hydrogen gas concentration of 0.1 to 18.3 vol % is supplied to a living organism.

2. An apparatus for supplying high-concentration hydrogen gas for a living organism, the apparatus comprising:
an electrolytic cell having an electrolytic chamber to which subject raw water is introduced, at least one membrane that separates inside and outside of the electrolytic chamber, and at least one pair of electrode plates provided in the inside and the outside of the electrolytic chamber so as to sandwich the membrane, one electrode plate in the outside of the electrolytic chamber being provided to be in contact with the membrane;
a direct-current power source that applies a direct-current voltage to the pair of electrode plates; and
a diluent gas supplier for diluting hydrogen gas generated from a cathode electrode plate of the electrode plates,
wherein the apparatus blows diluent gas supplied from the diluent gas supplier to a cathode water surface thereby to constantly maintain a hydrogen gas concentration measured at a position separated by 7 cm from the cathode water surface during electrolysis at lower than 18.3 vol % so that mixed gas comprising the hydrogen gas and the diluent gas and having a hydrogen gas concentration of 0.1 to 18.3 vol % is supplied to a living organism.

3. The apparatus for supplying high-concentration hydrogen gas for a living organism according to claim 1,
wherein the other electrode plate in the inside of the electrolytic chamber is also provided to be in contact with the membrane.

4. The apparatus for supplying high-concentration hydrogen gas for a living organism according to claim 1,
wherein the electrolytic chamber is provided with a diluent gas inlet that introduces the diluent gas from the diluent gas supplier and a mixed gas outlet that discharges the mixed gas;
wherein, in a state in which the subject raw water is introduced into the inside of the electrolytic chamber, the direct-current power source applies the direct-current voltage to both of the electrode plates using the one electrode plate provided outside the electrolytic chamber as an anode and the other electrode plate provided inside the electrolytic chamber as a cathode.

5. The apparatus for supplying high-concentration hydrogen gas for a living organism according to claim 1,
wherein a side chamber is provided outside the electrolytic chamber, and the side chamber encloses the one electrode plate in the outside of the electrolytic chamber.

6. The apparatus for supplying high-concentration hydrogen gas for a living organism according to claim 5,
wherein the side chamber is provided with a diluent gas inlet that introduces the diluent gas from the diluent gas supplier and a mixed gas outlet that discharges the mixed gas,
wherein, in a state in which the subject raw water is introduced into the inside of the electrolytic chamber, the direct-current power source applies the direct-current voltage to both of the electrode plates using the one electrode plate provided outside the electrolytic chamber as a cathode and the other electrode plate provided inside the electrolytic chamber as an anode.

7. The apparatus for supplying high-concentration hydrogen gas for a living organism according to claim 5,
wherein the subject raw water is introduced into the inside of the electrolytic chamber and the side chamber.

8. The apparatus for supplying high-concentration hydrogen gas for a living organism according to claim 1,
wherein the diluent gas is normal air.

9. The apparatus for supplying high-concentration hydrogen gas for a living organism according to claim 1,
wherein the diluent gas is blown at a flowing volume of 2 L/min or more.

10. The apparatus for supplying high-concentration hydrogen gas for a living organism according to claim 1,
wherein a chlorine gas concentration in the mixed gas is 1 ppm or less.

11. The apparatus for supplying high-concentration hydrogen gas for a living organism according to claim 1,
wherein the diluent gas supplier is operated at the same time when the direct-current voltage is applied or operated in advance thereof.

12. The apparatus for supplying high-concentration hydrogen gas for a living organism according to claim 2,
wherein the other electrode plate in the inside of the electrolytic chamber is also provided to be in contact with the membrane.

13. The apparatus for supplying high-concentration hydrogen gas for a living organism according to claim 2,
wherein the electrolytic chamber is provided with a diluent gas inlet that introduces the diluent gas from the diluent gas supplier and a mixed gas outlet that discharges the mixed gas;
wherein, in a state in which the subject raw water is introduced into the inside of the electrolytic chamber, the direct-current power source applies the direct-current voltage to both of the electrode plates using the one electrode plate provided outside the electrolytic chamber as an anode and the other electrode plate provided inside the electrolytic chamber as a cathode.

14. The apparatus for supplying high-concentration hydrogen gas for a living organism according to claim 2,
wherein a side chamber is provided outside the electrolytic chamber, wherein the side chamber encloses the one electrode plate in the outside of the electrolytic chamber.

15. The apparatus for supplying high-concentration hydrogen gas for a living organism according to claim 14,
wherein the side chamber is provided with a diluent gas inlet that introduces the diluent gas from the diluent gas supplier and a mixed gas outlet that discharges the mixed gas,
wherein, in a state in which the subject raw water is introduced into the inside of the electrolytic chamber, the direct-current power source applies the direct-current voltage to both of the electrode plates using the one electrode plate provided outside the electrolytic chamber as a cathode and the other electrode plate provided inside the electrolytic chamber as an anode.

16. The apparatus for supplying high-concentration hydrogen gas for a living organism according to claim 14,
wherein the subject raw water is introduced into the inside of the electrolytic chamber and the side chamber.

17. The apparatus for supplying high-concentration hydrogen gas for a living organism according to claim 2,
wherein the diluent gas is normal air.

18. The apparatus for supplying high-concentration hydrogen gas for a living organism according to claim 2,
wherein the diluent gas is blown at a flowing volume of 2 L/min or more.

19. The apparatus for supplying high-concentration hydrogen gas for a living organism according to claim 2, wherein a chlorine gas concentration in the mixed gas is 1 ppm or less.

20. The apparatus for supplying high-concentration hydrogen gas for a living organism according to claim 2, wherein the diluent gas supplier is operated at the same time when the direct-current voltage is applied or operated in advance thereof.

* * * * *